(12) United States Patent
Barrows et al.

(10) Patent No.: US 10,502,979 B2
(45) Date of Patent: Dec. 10, 2019

(54) IMPEDANCE SENSING CIRCUITS FOR OPHTHALMIC DEVICES

(71) Applicant: Johnson & Johnson Vision Care, Inc., Jacksonville, FL (US)

(72) Inventors: Corey Kenneth Barrows, Colchester, VT (US); Steven Philip Hoggarth, Cary, NC (US); Scott Robert Humphreys, Greensboro, NC (US); John Rocco Robillotto, Tarrytown, NY (US); Adam Toner, Jacksonville, FL (US); George A. Zikos, Riverdale, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 138 days.

(21) Appl. No.: 15/386,028

(22) Filed: Dec. 21, 2016

(65) Prior Publication Data

US 2018/0173012 A1    Jun. 21, 2018

(51) Int. Cl.
*G02C 7/08* (2006.01)
*A61B 5/0496* (2006.01)
(Continued)

(52) U.S. Cl.
CPC ............ *G02C 7/083* (2013.01); *A61B 5/0496* (2013.01); *A61B 5/053* (2013.01); *A61B 5/6821* (2013.01);
(Continued)

(58) Field of Classification Search
CPC .......... G02C 7/04; G02C 7/083; G02C 7/101; G02C 7/049; G02C 11/10; G02C 2202/20;
(Continued)

(56) References Cited

U.S. PATENT DOCUMENTS

| | | | | |
|---|---|---|---|---|
| 4,797,670 A | * | 1/1989 | Joyner | ..................... G05B 9/03 340/3.71 |
| 2010/0331977 A1 | * | 12/2010 | Schaper, Jr. | ....... A61B 5/04001 623/6.37 |

(Continued)

FOREIGN PATENT DOCUMENTS

EP      2687898      5/2019

OTHER PUBLICATIONS

K. Nagaraj et al: "Reduction of finite-gain effect in switched-capacitor filters", Electronics Letters, vol. 21, No. 15, Jan. 1, 1985 (Jan. 1, 1985), p. 644, XP055475685, GB ISSN: 0013-5194, DOI: 10.1049/el:19850457 Abstract; Introduction; Principle of Operation; Simulation Results.

(Continued)

*Primary Examiner* — Evan P Dzierzynski
*Assistant Examiner* — Sharrief I Broome

(57) ABSTRACT

The present disclosure relates to sensor systems for electronic ophthalmic devices. In certain embodiments, the sensor systems may comprise a sensor such as an adjustable resistor configured in series with an eye of a user of the electronic ophthalmic device. The sensor systems may comprise a gain stage configured to amplify a signal indicative of a difference between a voltage drop across the eye and the adjustable resistor. The sensor systems may comprise an integrator configured to integrate the amplified signal. A resistance value of the adjustable resistor is configured to cancel a DC component of a resistance of the eye when an electrical current is caused to flow through the eye and the adjustable resistor. As such, the configured resistance value of the adjustable resistor is indicative of an impedance of the eye.

24 Claims, 5 Drawing Sheets

(51) Int. Cl.
*G02C 7/04* (2006.01)
*A61F 2/16* (2006.01)
*A61F 2/14* (2006.01)
*A61B 5/053* (2006.01)
*A61B 5/00* (2006.01)

(52) U.S. Cl.
CPC ............ *A61B 5/7225* (2013.01); *A61F 2/145* (2013.01); *A61F 2/1624* (2013.01); *A61F 2/1635* (2013.01); *G02C 7/049* (2013.01); A61B 5/7246 (2013.01); A61B 2560/0204 (2013.01)

(58) Field of Classification Search
CPC ................ G02C 7/022; G02C 2202/16; G02C 2202/22; G02C 2202/18; G02C 7/02; G02C 7/081; G02C 7/08; G02C 7/061; G02C 7/085; G02C 7/06; G02C 7/102; A61F 2/1624; A61F 2/16; A61F 2250/0002; A61F 2/1627; A61F 2/1635; A61F 2250/0001; A61F 2/1613; A61F 2/14; A61F 2/145; A61F 2/1648; A61F 2002/1696; A61F 2210/0076; A61F 2/141; A61F 2/142; A61F 2/1618; A61F 2/1654; H01L 2924/00; H01L 2924/0002; H01L 2924/00014; H01L 2224/13109; H01L 2224/48091; H01L 2924/10253; H01L 2224/48145; H01L 2924/00012; H01L 2924/0105; H01L 2924/013; H01L 2224/11312; H01L 2224/16225; H01L 2224/2919

See application file for complete search history.

(56) References Cited

U.S. PATENT DOCUMENTS

2014/0240656 A1*  8/2014  Pugh ................. G02C 7/04
                                          351/159.03
2014/0243971 A1*  8/2014  Pugh ................. G02C 7/04
                                          623/6.22
2016/0062150 A1*  3/2016  Sako ................. G02C 11/10
                                          351/158

OTHER PUBLICATIONS

EP Search Report for Application No: PCT/US2017/067807 dated May 29 2019.

* cited by examiner

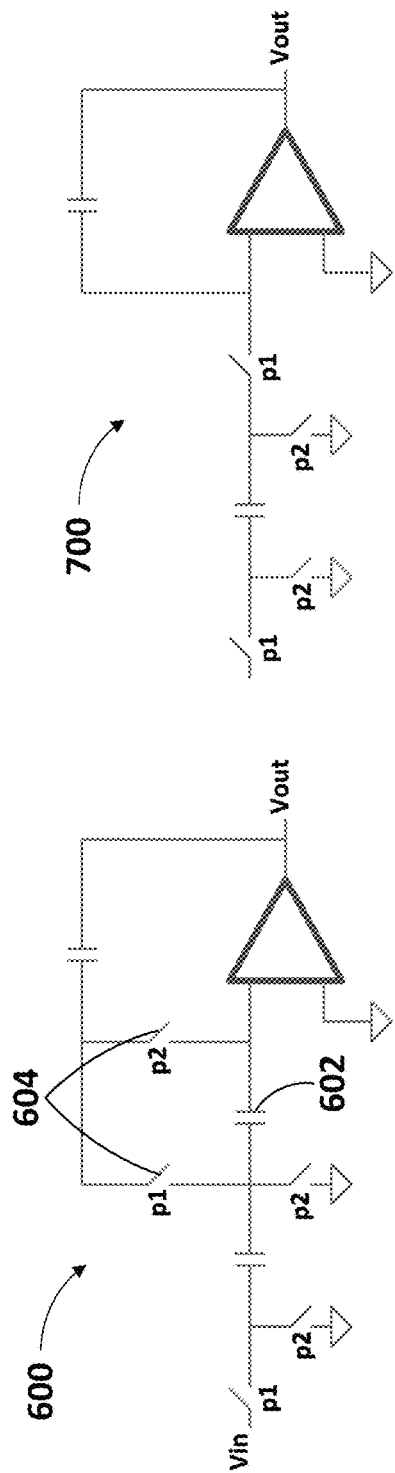
FIG. 6
FIG. 7
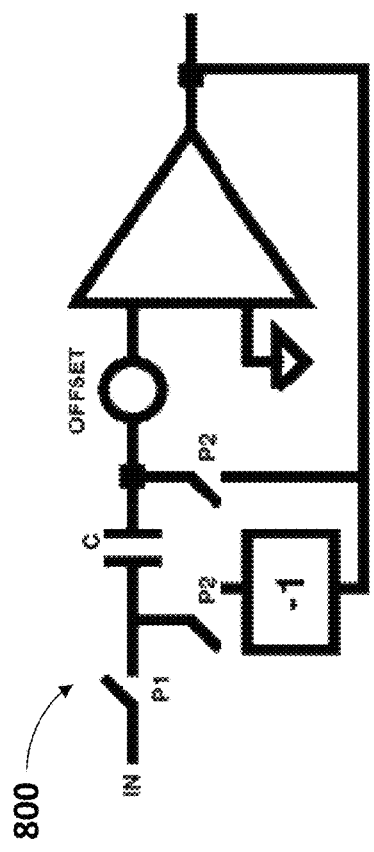
FIG. 8

IMPEDANCE SENSING CIRCUITS FOR OPHTHALMIC DEVICES

BACKGROUND OF THE DISCLOSURE

1. Field of the Disclosure

The present disclosure relates to electronic ophthalmic devices, such as wearable lenses, including contact lenses, implantable lenses, including intraocular lenses (IOLs) and any other type of device comprising optical components, and more particularly, to sensors and associated hardware and software for detecting ciliary muscle signals in an individual to activate and control electronic ophthalmic devices.

2. Discussion of the Related Art

Ophthalmic devices, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Ophthalmic devices may incorporate a lens assembly having an electronically adjustable focus to augment or enhance performance of the eye. In another example, either with or without adjustable focus, an ophthalmic devices may incorporate electronic sensors to detect concentrations of particular chemicals in the precorneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein.

Electronic and/or powered contract lenses may be designed to provide enhanced vision via zoom-in and zoom-out capabilities, or simply modify the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

Energy consumption, or more particularly current consumption, is also a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low-cost, long-term reliable service, safety and size while providing the required power.

In addition, because of the complexity of the functionality associated with a powered lens and the high level of interaction between all of its components, there is a need to coordinate and control the overall operation of the electronics and optics. Accordingly, there is a need for a system to control the operation the components that is safe, low-cost, and reliable, has a low rate of power consumption and is scalable for incorporation into ophthalmic devices.

SUMMARY OF THE DISCLOSURE

The present disclosure relates to powered ophthalmic devices that comprise an electronic system that, in turn, performs any number of functions, including actuating a variable-focus optic if included. The electronic system includes one or more batteries or other power sources, power management circuitry, one or more sensors, clock generation circuitry, control algorithms, circuitry comprising an impedance sensor, and lens driver circuitry.

Each eye contains a ciliary muscle, which is located around or proximate to the crystalline lens. Zonules attach to the ciliary muscle and, additionally, attach to the crystalline lens. The ciliary muscle controls accommodation for viewing objects at varying distances by changing the shape of the crystalline lens. For example, when focusing on a nearby object where a short focal distance is needed, the ciliary muscle contracts and slackens the zonules causing the crystalline lens to become rounder and more compressed.

As an example, when focusing on a distant object and a lengthened focal distance is needed, the ciliary muscle relaxes and the zonules pull on the edges of the crystalline lens causing it to be thinner and flatter. Accordingly, electrical signals derived from the changes in characteristics of the ciliary muscle may be utilized as a way to activate and control a powered ophthalmic device. As an example, when the ciliary muscle constricts and relaxes, the movement of the ciliary muscle and associated structures, such as the zonules, cause a change in impedance to current flowing through those structures, for example by altering the degree to which muscle fibers are oriented parallel/perpendicular to the flow of electrical current and hence changing the electrical impedance. This impedance and change in impedance may be indicative of a ciliary muscle characteristic such as a configuration of the muscle fibers.

Powered or electronic ophthalmic devices may have to account for the various ciliary muscle signals detected from an individual utilizing the powered or electronic ophthalmic devices. More specifically, powered ophthalmic devices may need to detect and differentiate between various ciliary muscle signals, and from one or more of other signals, noise, and interference.

The present disclosure relates to sensor systems for electronic ophthalmic devices. In certain embodiments, the sensor systems may comprise a sensor such as an adjustable resistor configured in series with an eye of a user of the electronic ophthalmic device. The sensor systems may comprise a gain stage configured to amplify a signal indicative of a difference between a voltage drop (e.g., IR drop) across the eye and the adjustable resistor. The sensor systems may comprise an integrator configured to integrate the amplified signal. A resistance value of the adjustable resistor is configured to cancel a direct current (DC) component of a resistance of the eye when an electrical current is caused to flow through the eye and the adjustable resistor. As such, the configured resistance value of the adjustable resistor is indicative of an impedance of the eye.

The present disclosure relates to electronic ophthalmic devices comprising one or more sensor systems described herein. In certain embodiments, an electronic ophthalmic device may comprise an ophthalmic lens having an optic zone and a peripheral zone. An ophthalmic device may comprise a variable optic element incorporated into the optic zone of the ophthalmic lens, the variable optic being configured to change the refractive power of the ophthalmic lens. An ophthalmic device may comprise an electronic component incorporated into the peripheral zone of the ophthalmic lens, the electronic component including the sensor system for detecting ciliary muscle movement associated with the process of accommodation, the sensor system configured to generate an action for controlling the variable-optic element.

The present disclosure relates to methods for sensing a characteristic of a ciliary muscle in a user of an ophthalmic device. In certain embodiments, a method may comprise causing an electrical current to flow through an eye of the user and an adjustable resistor configured in series with the eye of the user of the electronic ophthalmic device. A method may comprise amplifying a signal indicative of a difference between an IR drop across the eye and the adjustable resistor. A method may comprise integrating the amplified signal. A resistance value of the adjustable resistor is configured to cancel a DC component of a resistance of the eye when an electrical current is caused to flow through the eye and the adjustable resistor. Accordingly, the configured resistance value of the adjustable resistor is indicative of an impedance of the eye.

BRIEF DESCRIPTION OF THE DRAWINGS

The foregoing and other features and advantages of the disclosure will be apparent from the following, more particular description of preferred embodiments of the disclosure, as illustrated in the accompanying drawings.

FIG. 6 illustrates a schematic diagram of an exemplary integrator in accordance with some embodiments of the present disclosure.

FIG. 7 illustrates a schematic diagram of an exemplary integrator in accordance with some embodiments of the present disclosure.

FIG. 8 illustrates a schematic diagram of an exemplary out-of-bounds circuit in accordance with some embodiments of the present disclosure.

DETAILED DESCRIPTION OF THE PREFERRED EMBODIMENTS

Figure 1:
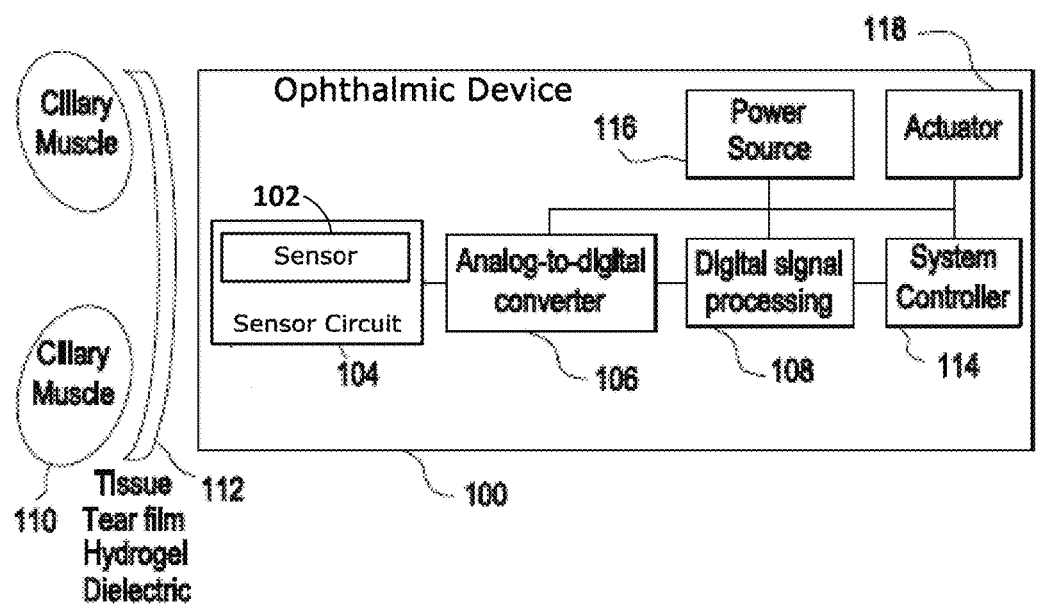
FIG. 1 illustrates an exemplary ophthalmic device comprising a sensor system in accordance with some embodiments of the present disclosure.

Ophthalmic devices may include contact lenses. Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The powered or electronic contact lens of the present disclosure comprises the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present disclosure may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present disclosure may be employed in a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may sense signals indicative of ciliary muscle movement, i.e. contraction and relaxation, to compensate for crystalline lens dysfunction or any other problems associated with visual acuity or eye disease. Based upon these signals, the powered ophthalmic lens may change state, for example, its refractive power, in order to either focus on a near object or a distant object. The ciliary muscle in the eye is the structure that controls or attempts to control the shape of the crystalline lens. The crystalline lens is encased in the capsule which is suspended by zonules connected to the ciliary muscle. The ciliary muscle causes the zonules to contract or to relax thereby changing the shape and/or focusing power of the crystalline lens. If the crystalline is unable to partially or fully respond to ciliary muscle movement, the individual will be unable to accommodate, a disease state known as presbyopia. Therefore, a powered or electronic ophthalmic lens that responds to these same signals may be utilized to compensate for this loss of ability to accommodate.

The iris, or colored part of the eye, is the partition between the anterior and posterior chambers of the eye and it is made up of two muscles that regulate the size of the pupil to control the amount of light entering the eye. The dilator muscle opens the pupil and the sphincter muscle closes the pupil. The eye also has six extraocular muscles that control the overall movement of the eye or eye globe. The sensing of the extraocular muscles and/or the dilator and sphincter muscles may provide other or additional functionality for a powered or electronic ophthalmic lens. The eye comprises a number of liquid components, including the tear film. These liquids are excellent conductors of electrical signals as well as other signals, such as acoustic signals or sound waves. Accordingly, it should be understood that a neuromuscular sensor in accordance with the present disclosure may provide feedback signals for controlling any number of functions that may be implemented by a powered or electronic ophthalmic lens. However, in accordance with the present disclosure, the circuitry is configured to detect, isolate and amplify ciliary muscle signals while filtering out noise and other muscle signals.

A sensor, the components of which may be embedded in a powered contact lens, may detect characteristics of different eye muscle signals. For example, various signals may include one or more of when an eye is moving up or down, focusing up close, and adjusting to a change in ambient light levels, such as from light to dark, dark to light or any other light condition. The ciliary muscle only controls the shape of the crystalline lens in order to focus on a near or distant object. The sensor relies on tracking various signals, including amplitude, time-domain response and frequency composition, produced by or emitted from the ciliary muscle in certain sample conditions, such as when an individual is reading, focusing far away, or in a room with fluorescent lighting. It is important to note that this list of conditions is exemplary and not exhaustive.

These ciliary muscle signal samples may be logged and tracked wherein the various waveforms and frequencies of each of the signals may be distinguished from one or more of other signals, noise, and interference. As set forth above, the circuitry of the present disclosure is preferably designed to detect, isolate and/or filter ciliary muscle signals. In alternate embodiments, other muscle signals may be utilized for augmenting or implementing other ocular functions. Whenever the sensor detects a recognized ciliary muscle signal, it may trigger activity in the electronic circuitry, for example, activating an electronic lens.

As set forth herein, the crystalline lens of the eye is suspended by zonules, the fibers that are attached to both the crystalline lens and the ciliary muscle. The ciliary muscle reacts to various stimuli and sends out any number of signals that are normally interpreted by the central nervous system whereupon some action takes place. For example, in accommodation, when the retina receives an image from a close or near object, the ciliary muscle contracts. This contraction causes the zonules to relax and allows the crystalline lens to thicken which in turn makes the lens stronger (adding plus power) which is needed to focus on a close up or near object. This process is known as accommodation. More specifically, this is one of the more widely accepted theories of how the ciliary muscle works in conjunction with the zonules and the crystalline lens in accommodation. In individuals with presbyopia, the crystalline lens becomes less flexible, and thus may not move regardless of the ciliary muscle contraction. Even though the crystalline lens does not respond, the ciliary muscle still contracts or otherwise reacts and sends out a measurable signal and this measurable signal may be utilized with a powered lens to compensate for the lack of response by the crystalline lens. In other words, regardless of the theory of how the precise mechanism of accommodation works relative to the ciliary muscle, the ciliary muscle does react to different stimuli and thus its response may be measured with the right sensors. Accordingly, a complete set of ciliary muscle responses may be measured under various conditions or stimuli and a set of data developed to be utilized as a set of feedback signals for controlling a powered or electronic ophthalmic lens directly. The powered or electronic ophthalmic lens may be utilized to compensate for various visual acuity problems, including presbyopia, as well as any number of other conditions.

There may be various methods used to implement some exemplary embodiments of the present disclosure. For example, sensors may detect a ciliary muscle signal utilizing one or more of electromyography (EMG), magnetomyography (MMG), phonomyography (PMG), and impedance. Furthermore, sensors may comprise a non-contact sensor, such as an antenna that is embedded into a contact lens, but that does not directly touch the surface of an eye. Alternately, sensors may comprise a contact sensor, such as contact pads that directly touch the surface of an eye. It is important to note that any number of suitable devices and processes may be utilized for the detection of signals from the ciliary muscle as is explained in detail subsequently. As described herein, any type of sensor and/or sensing technology may be utilized. In accordance with an alternate exemplary embodiment, ultrasound biomicroscopy may be utilized to image the ciliary body region of the eye. With ultrasound biomicroscopy, it is possible to distinguish and analyze the changes in the ciliary muscle contour in different accommodation states. Since changes in ciliary muscle contour may be detected in this manner, the results or changes may be provided to and utilized in accordance with the present disclosure in the same manner as any other sensing device.

In certain embodiments, ophthalmic devices may comprise one or more sensor systems, such as circuits. The sensor systems may be configured to cause an electrical current to flow through an eye of a wearer of the ophthalmic device(s) and one or more adjustable resistors. As an example, the adjustable resistors may comprise programmable resistors. As a further example, the one or more adjustable resistors may be configured in series with the eye. As such, when the wearer attempts to change the focal length of their eye, the sensor system determines (e.g., measures) a change in the impedance of the eye. As an illustrative example, an error signal may be created by the sensor systems when an IR drop across the adjustable resistor(s) is subtracted from IR drop across the eye. The error signal may be integrated and the values of the adjustable resistor(s) may be modified to minimize the error signal. Accordingly, the value of the adjustable resistor(s) may be indicative of the impedance across the eye, which may also represent a characteristic of the ciliary muscle.

FIG. 1 illustrates, in block diagram form, an ophthalmic device 100 disposed on the front surface of the eye or cornea 112, in accordance with one exemplary embodiment of the present disclosure. Although the ophthalmic device 100 is shown and described as a being disposed on the front surface of the eye, it is understood that other configurations, such as those including intraocular lens configuration may be used. In this exemplary embodiment, the sensor system may comprise one or more of a sensor 102, a sensor circuit 104, an analog-to-digital converter 106, a digital signal processor 108, a power source 116, an actuator 118, and a system controller 114. As illustrated, the ciliary muscle 110 is located behind the front eye surface or cornea 112. More specifically, the globe of the eye can be divided into two segments; namely, the anterior chamber and the posterior chamber. The iris is the partition between the anterior and posterior chambers. Between the front surface of the crystalline lens and the back surface of the iris is the posterior chamber. At the base of the iris is the ciliary body which produces aqueous humor and is continuous with the ciliary muscle. The ophthalmic device 100 is placed onto the front surface of the eye 112 wherein the electronic circuitry of the sensor system may be utilized to implement the neuromuscular sensing of the present disclosure. The sensor 102 as well as the other circuitry is configured to sense signals from ciliary muscle 110 actions through the various tissue and liquids forming the eye and produced by the eye. As set forth above, the various fluids comprising the eye are good conductors of electrical and acoustical signals.

In this exemplary embodiment, the sensor 102 may be at least partially embedded into the ophthalmic device 100. The sensor 102 may be in electrical communication with the eye, for example in series with the eye. The sensor 102 may be or comprise one or more adjustable resistors such as programmable resistors. The sensor 102 may be configured to receive an electrical current flowing through the eye. As such, when the impedance of the eye changes, for example, due to a change in characteristics of the ciliary muscle, the sensor 102 may be configured to the change in characteristics of the ciliary muscle. For example, there may be various signals detected by the sensor 102 depending on the state that a ciliary muscle is in, such as whether it is contracting or relaxing, or on the type of action that a ciliary muscle is trying to perform, such as causing the eye to focus on a near object or a far object.

The sensor circuit 104 or sensor system may be configured to process signals received by the sensor 102. As an example, the sensor circuit 104 may be configured to amplify a signal to facilitate integration of small changes in signal level. As a further example, the sensor circuit 104 may be configured to amplify a signal to a useable level for the remainder of the system, such as giving a signal enough power to be acquired by various components of the sensor circuit 104 and/or the analog-to-digital converter 106. In addition to providing gain, the sensor circuit 104 may include other analog signal conditioning circuitry such as filtering and impedance matching circuitry appropriate to the sensor 102 and sensor circuit 104 output. The sensor circuit 104 may comprise any suitable device for amplifying and conditioning the signal output by the sensor 102. For example, the sensor circuit 104 may simply comprise a single operational amplifier or a more complicated circuit comprising one or more operational amplifiers. As described in further detail in FIG. 3, the sensor circuit 104 may be configured to determine (e.g., measures) a change in the impedance of the eye. As an illustrative example, an error signal may be created by the sensor circuit 104 when an IR drop across the sensor 102 is subtracted from IR drop across the eye. The error signal may be integrated and the resistance value of the sensor 102 may be modified to minimize the error signal. Accordingly, the resistance value of the sensor 102 may be indicative of the impedance across the eye, which may also represent a characteristic of the ciliary muscle. As set forth above, the sensor 102 and the sensor circuit 104 are configured to capture and isolate the signals indicative of characteristic of the ciliary muscle from the noise and other signals produced in or by the eye and convert it to a signal usable ultimately by the system controller 114. The system controller 114 is preferably preprogrammed to recognize the various signals produced by the ciliary muscle under various conditions and provide an appropriate output signal to the actuator 118.

In this exemplary embodiment, the analog-to-digital converter 106 may be used to convert an analog signal output from the amplifier into a digital signal for processing. For example, the analog-to-digital converter 106 may convert an analog signal output from the sensor circuit 104 into a digital signal that may be useable by subsequent or downstream circuits, such as a digital signal processing system 108 or microprocessor. A digital signal processing system or digital signal processor 108 may be utilized for digital signal processing, including one or more of filtering, processing, detecting, and otherwise manipulating/processing sampled data to discern a ciliary muscle signal from noise and interference. The digital signal processor 108 may be preprogrammed with the ciliary muscle responses described above. The digital signal processor 108 may be implemented utilizing analog circuitry, digital circuitry, software and/or preferably a combination thereof. For example, various ciliary muscle signals that may occur within a certain frequency range may be distinguishable from other signals, noise, and interference that occur within other frequency ranges. Certain commonly occurring noise and interference signals may be notched at various stages in the signal acquisition chain utilizing analog or digital filters, for example, harmonics of $^{50}/_{60}$ Hz AC mains and fluorescent lights.

A power source 116 supplies power for numerous components comprising the non-contact sensor system. The power may be supplied from a battery, energy harvester, or other suitable means as is known to one of ordinary skill in the art. Essentially, any type of power source may be utilized to provide reliable power for all other components of the system. A ciliary muscle signal, processed from analog to digital, may enable activation of the system controller 114. Furthermore, the system controller 114 may control other aspects of a powered contact lens depending on input from the digital signal processor 108, for example, changing the focus or refractive power of an electronically controlled lens through an actuator 118.

In further alternate exemplary embodiments, the system controller 114 may receive input from sources including one or more of a contact sensor, a blink detector, and a fob control. By way of generalization, it may be obvious to one skilled in the art that the method of activating and/or controlling the system controller 114 may require the use of one or more activation methods. For example, an electronic or powered contact lens may be programmable specific to an individual user, such as programming a lens to recognize both of an individual's ciliary muscle signals when performing various actions, for example, focusing on an object far away, or focusing on an object that is near, and an individual's blink patterns. In some exemplary embodiments, using more than one method to activate an electronic contact lens, such as ciliary muscle signal detection and blink detection, may give the ability for each method to crosscheck with another before activation of the contact lens occurs. An advantage of crosschecking may include mitigation of false positives, such as minimizing the chance of unintentionally triggering a lens to activate.

In one exemplary embodiment, the crosschecking may involve a voting scheme, wherein a certain number of conditions are met prior to any action taking place. The actuator 118 may comprise any suitable device for implementing a specific action based upon a received command signal. The actuator 118 may comprise an electrical device, a mechanical device, a magnetic device or any combination thereof. The actuator 118 receives a signal from the system controller 114 in addition to power from the power source 116 and produces some action based on the signal from the system controller 114. For example, if the system controller 114 signal is indicative of the wearer trying to focus on a near object, the actuator 118 may be utilized to somehow change the refractive power of the electronic ophthalmic lens.

Figure 2:
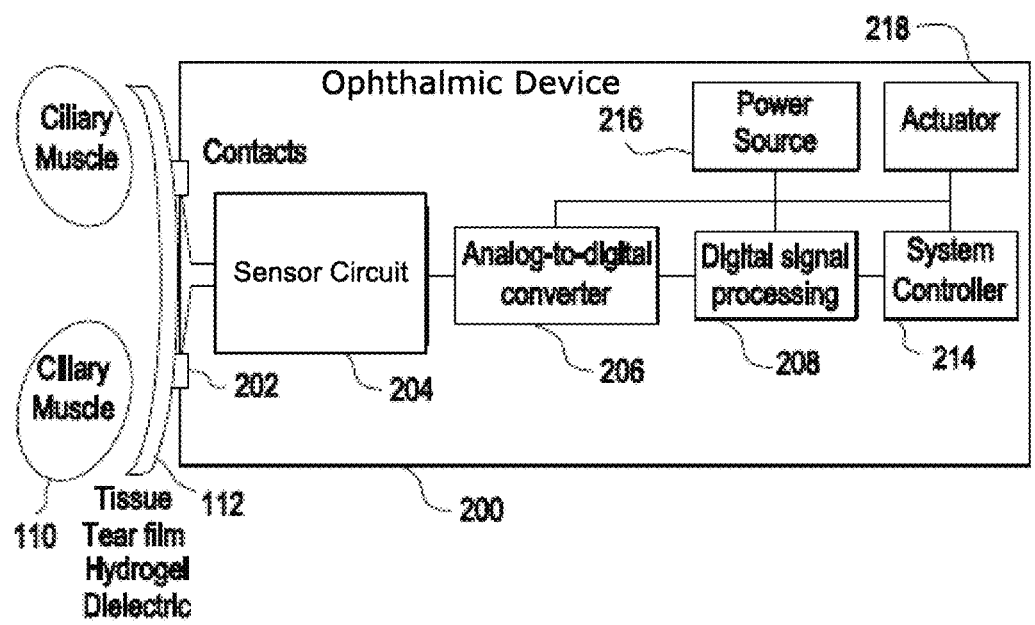
FIG. 2 illustrates an exemplary ophthalmic device comprising a sensor system in accordance with some embodiments of the present disclosure.

FIG. 2 illustrates an ophthalmic device 200, comprising a sensor system, shown on the front surface of the eye or cornea 112 in accordance with another exemplary embodiment of the present disclosure. In this exemplary embodiment, a sensor system may comprise a contact or multiple contacts 202, a sensor circuit 204, an analog-to-digital converter 206, a digital signal processor 208, a power source 216, an actuator 218, and a system controller 214. The ciliary muscle 110 is located behind the front eye surface or cornea 112. The ophthalmic device 200 is placed onto the front surface of the eye 112, such that the electronic circuitry of the sensor may be utilized to implement the neuromuscular sensing of the present disclosure. The components of this exemplary system are similar to and perform the same functions as those illustrated in FIG. 1, with the exception of contacts 202 and the sensor circuit 204. In other words, since direct contacts 202 are utilized, there is no need for an antenna or an amplifier to amplify and condition the signal received by the antenna.

In the illustrated exemplary embodiment, the contacts 202 may provide for a direct electrical connection to the tear film and the eye surface. For example, the contacts 202 may be implemented as metal contacts that are exposed on the back curve of the ophthalmic device 200 and be made of biocompatible conductive materials, such as gold or titanium. Furthermore, the contact lens polymer may be molded around the contacts 202, which may aid in comfort on the eye and provide improved conductivity through the ophthalmic device 200. Additionally, the contacts 202 may provide for a low resistance connection between the eye's surface 112 and the electronic circuitry within the ophthalmic device 200. Four-terminal sensing, also known as Kelvin sensing, may be utilized to mitigate contact resistance effects on the eye. The sensor circuit 204 may emit a signal with several constituent frequencies or a frequency sweep, while measuring the voltage/current across the contacts 202.

In an alternate exemplary embodiment, the sensor circuit 204 may be configured to read a potential difference across the eye arising from a voltage or current produced by the contraction or relaxation of the ciliary muscle 110. It is important to note that various types of sensors may be utilized, given that the eye comprises various fluids, including tears which are excellent conductors. The sensor circuit 204 may be configured to measure the impedance of an eye wherein the impedance may change in a certain location based upon what a ciliary muscle is trying to do, such as contracting or relaxing. In this exemplary embodiment, the analog-to-digital converter 206 and the digital signal processing 208 may be configured differently for a contact-based sensor as opposed to a non-contact based sensor, as described in FIG. 1. For example, there may be a different sample rate, a different resolution, and different signal processing algorithm 208.

Figure 3:
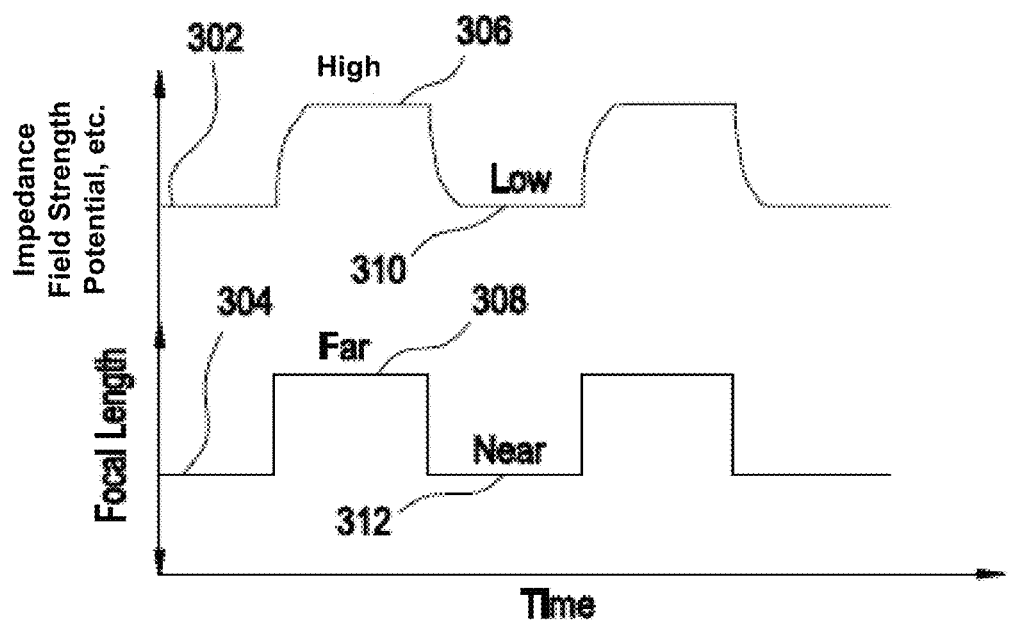
FIG. 3 is a graphical representation demonstrating correlations between measurable electrical parameters and the eye's desired focal length in accordance with the present disclosure.

FIG. 3 illustrates a graph demonstrating correlations between measurable electrical parameters and the eye's focal length as described in the referenced literature. Trace 302 is a representation of an electrically measurable signal in or on the eye. For example, such signals may be detected as one or more of impedance, voltage potential, induced electromagnetic field, and other measurable parameters. Trace 304 is a representation of a desired focal length wherein for example, if clinical subjects focused on objects at 0.2 and 2.0 meter distances, the ciliary muscle may undergo a corresponding change in measurable electrical parameters accordingly, depending on the distance of focus. However, using the same example, the actual focal length of a lens may not change or only changes minimally, such as in cases where a person may be presbyopic and the lens of the eye is too rigid and unable to accommodate for a change in focus, even where the ciliary muscles are responding to the change.

As described in the literature, there is a correlation between a measurable electrical signal and a focal length. As illustrated in FIG. 3, impedance is high 306 when the focal length is far 308 and impedance is low 310 when the focal length is near 312. Additionally, as described in the literature but not illustrated in FIG. 3, a correlation exists between the amplitude of traces 302 and 304 for intermediate values.

In some exemplary embodiments, characteristics of an electrical signal (e.g., trace 302, 304) such as shape, frequency content, timing, and amplitude, may vary due to several factors including one or more of a detection method utilized (e.g., impedance or field strength), an individual's eye physiology, ciliary muscle fatigue, electrolyte levels in the eye, state of presbyopia, interference, and focal length. For example, depending on the type of detection method used, the correlation between desired focus and measurable electrical parameter may have the opposite polarity from what is illustrated in FIG. 3.

Additionally, for example, an electrical signal may be distorted from carrying one or more of significant noise, interference from other muscles, and interference from various environmental sources or due to the effects of aging, disease or genetics. Accordingly, studies of eye response and individual user measurement and training may be used to program the digital signal circuitry to properly detect the eye's desired focal length. Parameters of the digital signal processing may be adjusted in response to other measurements, for example, time of day, measured electrolyte levels, ambient light levels and the like. Furthermore, recorded samples of a user's eye focus signals may be used in conjunction with interference detection and mitigation techniques. It is important to note that any type of sensor may be utilized in accordance with the present disclosure. As long as there is muscle movement associated with changing conditions, it may be sensed, processed and utilized to enhance, augment or simply provide vision correction.

Figure 4:
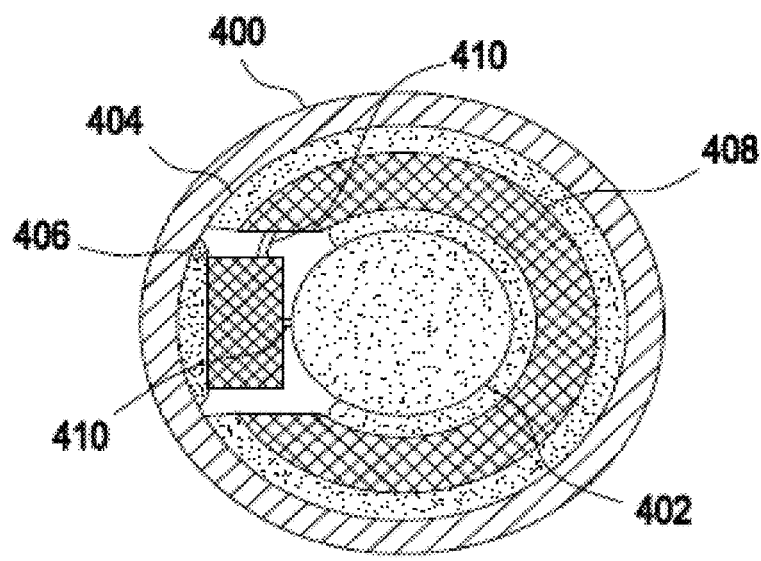
FIG. 4 is a planar view of an ophthalmic device comprising electronic components, including a sensor system and a variable-optic element in accordance with the present disclosure.

Referring now to FIG. 4, there is illustrated, in planar view, a wearable electronic ophthalmic device comprising a sensor in accordance with the present disclosure. The ophthalmic device 400 comprises an optic zone 402 and a peripheral zone 404. The optic zone 402 may function to provide one or more of vision correction, vision enhancement, other vision-related functionality, mechanical support, or even a void to permit clear vision. In accordance with the present disclosure, the optic zone 402 may comprise a variable optic element configured to provide enhanced vision at near and distant ranges based on signals sensed from the ciliary muscle. The variable-optic element may comprise any suitable device for changing the focal length of the lens or the refractive power of the lens based upon activation signals from the sensing system described herein. For example, the variable optic element may be as simple as a piece of optical grade plastic incorporated into the lens with the ability to have its spherical curvature changed. The peripheral zone 404 comprises one or more of electrical circuits 406, a power source 408, electrical interconnects 410, mechanical support, as well as other functional elements.

The electrical circuits 406 may comprise one or more integrated circuit die, printed electronic circuits, electrical interconnects, and/or any other suitable devices, including the sensing circuitry described herein. The power source 408 may comprise one or more of battery, energy harvesting, and or any other suitable energy storage or generation devices. It is readily apparent to the skilled artisan that FIG. 4 only represents one exemplary embodiment of an electronic ophthalmic lens and other geometrical arrangements beyond those illustrated may be utilized to optimize area, volume, functionality, runtime, shelf life as well as other design parameters. It is important to note that with any type of variable optic, the fail-safe is distance vision. For example, if power were to be lost or if the electronics fail, the wearer is left with an optic that allows for distance vision.

Figure 5:
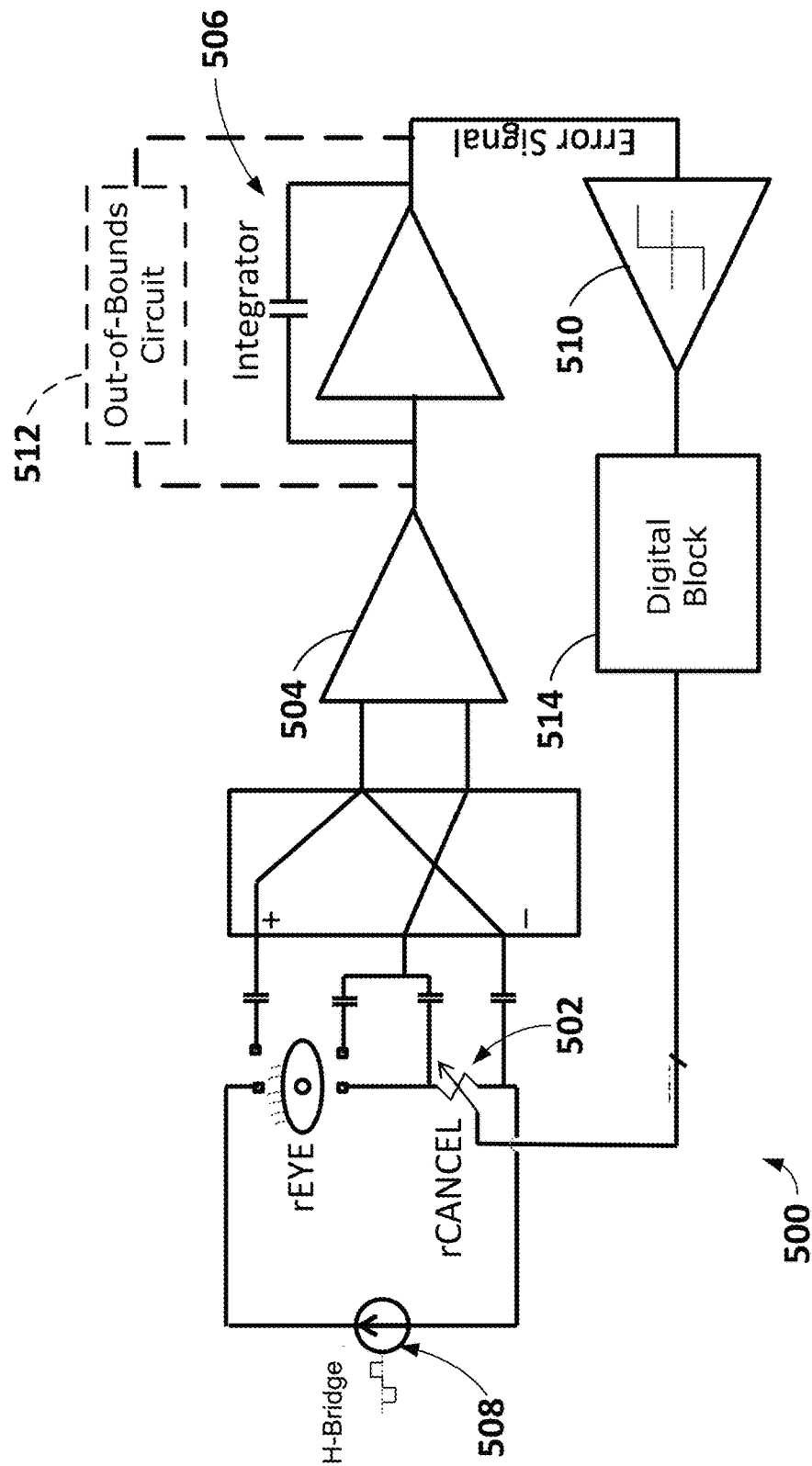
FIG. 5 is a block diagram of an exemplary sensor system in accordance with some embodiments of the present disclosure.

FIG. 5 illustrates a sensor system 500 (e.g., circuit) in accordance with one exemplary embodiment of the present disclosure. The sensor system 500 may be at least partially integrated with an electronic ophthalmic device. The sensor system 500 may comprise a sense resistor or sensor 502, a gain stage 504, and an integrator 506. The sense resistor or sensor 502 may be configured in series with an eye of a wearer of the electronic ophthalmic device. The sensor 502 may be or comprise an adjustable resistor or resistors. The sensor 502 may comprise a plurality of resistors configured as parallel binary weighted resistors. Resistor sizing may be configured for matching by using multiples of longer unit sized devices. For example, instead of configuring parallel resistors in steps of 1-2-4-8 (15 total steps) by stepped size, the parallel configuration may be single size unit steps (e.g., 15 single unit steps) in parallel. As such, the total value of resistance of the sensor 502 is provided with increased resolution. The resistance value of the sensor 502 may be modified using steps having fixed or variable value. As an example, a step size of the resistance value of the sensor 502 may increase with total impedance. As a further example, the step size of the sensor 502 may be adjusted based on the following relationship:

$$\text{Sensor Step Size} = \text{Sensor resistance value} - \left(\frac{1}{\text{Sensor resistance value}} + \frac{1}{RSLB}\right)^{-1}$$

However, other target resistance values and formulas may be used to manage the step sizes.

The gain stage 504 may be configured to amplify a signal indicative of a difference between an IR drop across the eye (rEYE) and the resistance value (rCANCEL) of the sensor 502. The gain stage 504 may be configured to autozero based upon a predetermined time such as a particular phase. The gain stage 504 may be or comprise a differential amplifier.

The integrator 506 may be configured to integrate the amplified signal. The integrator 506 may be or comprise an integrator circuit as illustrated in each of FIGS. 6-7. As an example, the integrator 506 may be or comprise a Nagaraj integrator 600, as illustrated in FIG. 6. As shown, the Nagaraj integrator may comprise a capacitor 602 and switches 604 disposed at the amplifier input to compensate for offsets and finite gain. However, other integrator configuration may be used, such as the integrator 700 illustrated in FIG. 7.

In an embodiment, the sensor system 500 may comprise an H-bridge 508 configured to direct and/or receive an electrical current through the eye and/or the sensor 502. As an example, the H-bridge 508 may be configured to control electrical current through a series configuration of the eye (rEYE) and the sensor 502 (rCANCEL). The sensor system 500 may comprise a comparator 510 configured to determine whether the input (e.g., error signal) from the integrator 506 is positive or negative.

In an embodiment, the sensor system 500 may comprise an out-of-bounds circuit 512 configured to detect an output of the integrator 506 that exceeds a predetermined threshold. The threshold can be adjusted and may be a function of the offset of the integrator 506. As an example, the out-of-bounds circuit 512 comprises an operational amplifier with systematic offset, such as illustrated in FIG. 8. Other configurations may be used.

The sensor system 500 may comprise a digital block 514 comprising a digital-to-analog converter. The digital block 514 may be configured to function as a first order sigma-delta (SD) filter. As an example, the digital block 514 may be configured to average (e.g., low pass filtering) the value (rCANCEL) of the sensor 502 to yield improved resolution for the impedance (rEYE) of the eye. The digital block 514 may be configured to monitor outputs of one or more of the integrator 506 and the out-of-bounds circuit 512 and to determine (e.g., calculate) a value (rCANCEL) of the sensor 502 to minimize the integrated system error. As an illustrative example, the digital block 514 may be configured to increase the rCANCEL code when the output of the integrator 506 is less than 0 and to decrease the rCANCEL code when the output of the integrator 506 is greater than 0. As a further example, to smooth rCANCEL hunting (e.g., modification of the value of the sensor 502) each step in one direction reduces the step size in the same direction. The step reduction may be limited, for example, to 1/16 and the reduction may be cancelled when the comparator of integrator 506 and/or the out-of-bounds circuit 512 changes directions. To increase rCANCEL lock speed the out-of-bounds circuit 512 may be configured to monitor the output of the integrator 506. When the output of the integrator 506 is larger than the predetermined threshold (e.g., ~50 mV) defined by the out-of-bounds circuit 512, the rCANCEL may be adjusted as a binary search step to find a value that does not accumulate large integrator outputs such as those exceeding the predetermined threshold. The size of the binary steps may be reduced each time a binary step is made. When a binary step is made the integrator 506 may be temporarily zeroed out.

In operation, an adjustment of the resistance value of the sensor 502 will result in a change in the output of the integrator 506. As an example, the resistance value of the sensor 502 may be configured to cancel the IR drop across the eye such that the output of the integrator is minimized. Once the integrator output is minimized, the configured resistance value of the adjustable resistor may be indicative of an impedance of the eye. As an illustrative example, the sensor 502 may be or comprise an adjustable resistor and a resistance value of the adjustable resistor may be configured based upon the difference between IR drop across the eye and the adjustable resistor. In particular, the resistance value of the adjustable resistor may be configured minimize the difference between IR drop across the eye and the adjustable resistor.

Figure 9:
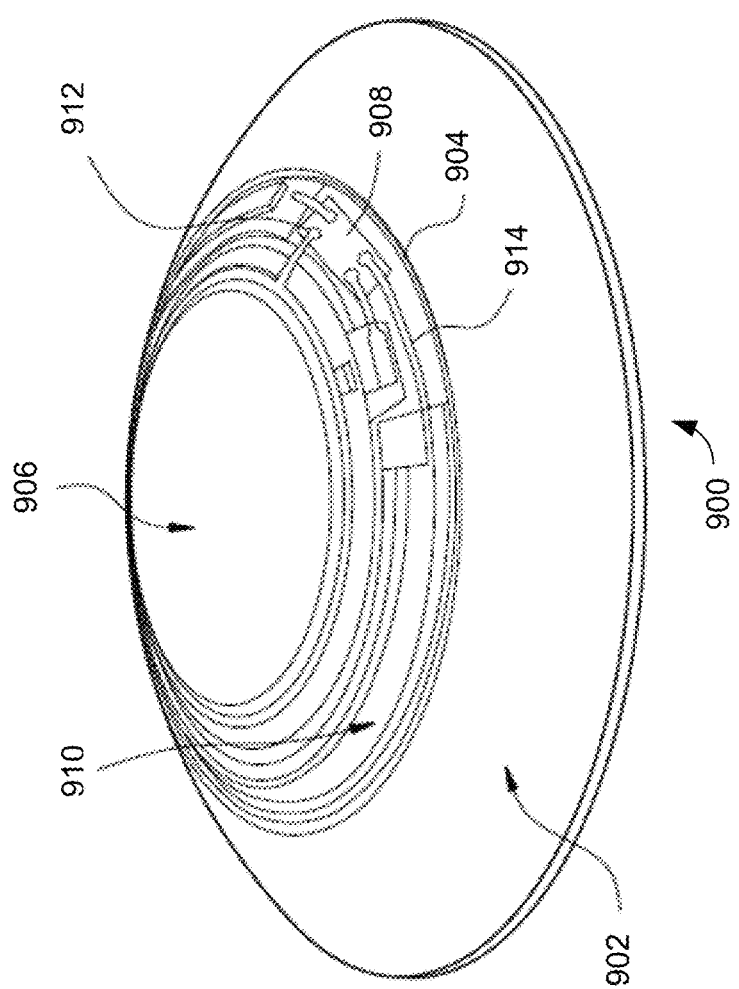
FIG. 9 is a diagrammatic representation of an exemplary powered or electronic ophthalmic device in accordance with the present disclosure.

FIG. 9 is a diagrammatic representation of an exemplary electronic insert, including a combined blink detection and communication system, positioned in a powered or electronic ophthalmic device in accordance with the present disclosure. As shown, a contact lens 900 comprises a soft plastic portion 902 which comprises an electronic insert 904. This insert 904 includes a lens 906 which is activated by the electronics, for example, focusing near or far depending on activation. Integrated circuit 908 mounts onto the insert 904 and connects to batteries 910, lens 906, and other components as necessary for the system. The integrated circuit 908 includes a sensor 912 and associated signal path circuits. The sensor 912 may comprise any sensor configuration such as those described herein. The sensor 912 may also be implemented as a separate device mounted on the insert 904 and connected with wiring traces 914.

Although shown and described in what is believed to be the most practical and preferred embodiments, it is apparent that departures from specific designs and methods described and shown will suggest themselves to those skilled in the art and may be used without departing from the spirit and scope of the disclosure. The present disclosure is not restricted to the particular constructions described and illustrated, but should be constructed to cohere with all modifications that may fall within the scope of the appended claims.

What is claimed is:

1. A sensor system for an electronic ophthalmic device, the sensor system comprising:
    an adjustable resistor configured in series with an eye of a user of the electronic ophthalmic device;
    a gain stage configured to amplify an error signal comprising a difference between a voltage drop across the eye and a voltage drop across the adjustable resistor; and
    an integrator configured to integrate the amplified signal, wherein a resistance value of the adjustable resistor is configured to cancel a DC component of a resistance of the eye when an electrical current is caused to flow through the eye and the adjustable resistor, and wherein the resistance value of the adjustable resistor is adjusted to decrease the error signal.

2. The sensor system according to claim 1, wherein the resistance value of the adjustable resistor is configured to minimize the error signal.

3. The sensor system according to claim 1, wherein the integrator comprises a Nagaraj integrator.

4. The sensor system according to claim 1, further comprising an out-of-bounds circuit configured to detect an output of the integrator that exceeds a predetermined threshold.

5. The sensor system according to claim 4, wherein the out-of-bounds circuit comprises an operational amplifier with systematic offset.

6. The sensor system according to claim 4, wherein the gain stage is configured to autozero in response to the output of the integrator exceeding a predetermined threshold.

7. The sensor system according to claim 1, further comprising an H-bridge configured to transmit an electrical current to the eye and/or receive an electrical current from the eye.

8. An ophthalmic device comprising the sensor system of claim 1.

9. The ophthalmic device of claim 8, wherein the ophthalmic device comprises a contact lens, an intraocular lens, an overlay lens, an ocular insert, or an optical insert, or a combination thereof.

10. An electronic ophthalmic device comprising the sensor system of claim 1, the electronic ophthalmic device comprising:
    an ophthalmic lens having an optic zone and a peripheral zone;
    a variable optic element incorporated into the optic zone of the ophthalmic lens, the variable optic being configured to change the refractive power of the ophthalmic lens; and
    an electronic component incorporated into the peripheral zone of the ophthalmic lens, the electronic component including the sensor system for detecting ciliary muscle movement associated with the process of accommodation, the sensor system configured to generate an action for controlling the variable-optic element.

11. The electronic ophthalmic lens according to claim 10, wherein the ophthalmic lens comprises a contact lens.

12. The electronic ophthalmic lens according to claim 11, wherein the contact lens is a soft or hybrid contact lens.

13. The electronic ophthalmic lens according to claim 10, wherein the sensing system comprises a power source, a signal processor, a controller, and an actuator.

14. The electronic ophthalmic lens according to claim 13, wherein the power source comprises a battery.

15. The electronic ophthalmic lens according to claim 13, wherein the signal processor comprises a digital signal processor.

16. The electronic ophthalmic lens according to claim 13, wherein the controller comprises a microprocessor.

17. The electronic ophthalmic lens according to claim 13, wherein the actuator is operatively associated with the variable-optic element.

18. A method for sensing a characteristic of a ciliary muscle in a user of an ophthalmic device, the method comprising:
    causing an electrical current to flow through an eye of the user and an adjustable resistor configured in series with the eye of the user of the ophthalmic device;
    amplifying an error signal comprising a difference between a voltage drop across the eye and a voltage drop across the adjustable resistor; and
    integrating the amplified signal, wherein a resistance value of the adjustable resistor is configured to cancel a DC component of a resistance of the eye when an electrical current is caused to flow through the eye and the adjustable resistor, and wherein the resistance value of the adjustable resistor is adjusted to decrease the error signal.

19. The method according to claim 18, wherein the resistance value of the adjustable resistor is configured to minimize the error signal.

20. The method according to claim 18, wherein the integrator comprises a Nagaraj integrator.

21. The method according to claim 18, further comprising an out-of-bounds circuit configured to detect an output of the integrator that exceeds a predetermined threshold.

22. The method according to claim 21, wherein the out-of-bounds circuit comprises an operational amplifier with systematic offset.

23. The method according to claim 18, wherein the gain stage is configured to autozero in response to the output of the integrator exceeding a predetermined threshold.

24. The method according to claim 18, wherein causing the electrical current to flow through an eye of the user and the adjustable resistor is implemented via an H-bridge.

* * * * *